(12) United States Patent
Giniger et al.

(10) Patent No.: US 9,289,362 B2
(45) Date of Patent: Mar. 22, 2016

(54) FOAMING COMPOSITIONS AND METHODS

(76) Inventors: Martin S. Giniger, New York, NY (US); Matthew S. Spaid, New York, NY (US)

( * ) Notice: Subject to any disclaimer, the term of this patent is extended or adjusted under 35 U.S.C. 154(b) by 2037 days.

(21) Appl. No.: 11/355,925

(22) Filed: Feb. 15, 2006

(65) Prior Publication Data

US 2006/0229226 A1    Oct. 12, 2006

Related U.S. Application Data (60) Provisional application No. 60/653,421, filed on Feb. 15, 2005, provisional application No. 60/734,549, filed on Nov. 7, 2005.

(51) Int. Cl.

| | | |
|---|---|---|
| *C11D 3/00* | (2006.01) |
| *A61K 8/365* | (2006.01) |
| *A61K 8/04* | (2006.01) |
| *A61K 8/19* | (2006.01) |
| *A61K 8/22* | (2006.01) |
| *A61K 8/38* | (2006.01) |
| *A61Q 11/00* | (2006.01) |
| *A61Q 19/02* | (2006.01) |

(52) U.S. Cl.
CPC .................. *A61K 8/365* (2013.01); *A61K 8/046* (2013.01); *A61K 8/19* (2013.01); *A61K 8/22* (2013.01); *A61K 8/38* (2013.01); *A61Q 11/00* (2013.01); *A61Q 19/02* (2013.01); *A61K 2800/222* (2013.01); *A61K 2800/88* (2013.01)

(58) Field of Classification Search
None
See application file for complete search history.

(56) References Cited

U.S. PATENT DOCUMENTS

| | | | | |
|---|---|---|---|---|
| 4,347,331 A | * | 8/1982 | Self | 521/119 |
| 4,383,987 A | * | 5/1983 | Kiozpeoplou | 424/49 |
| 4,487,757 A | * | 12/1984 | Kiozpeoplou | 424/49 |
| 5,023,074 A | * | 6/1991 | Morton et al. | 424/52 |
| 5,766,574 A | * | 6/1998 | Christina-Beck et al. | 424/53 |
| 5,988,444 A | * | 11/1999 | Williams et al. | 222/137 |
| 2002/0187108 A1 | * | 12/2002 | Rajaiah et al. | 424/49 |
| 2003/0003059 A1 | * | 1/2003 | Dana | 424/49 |
| 2005/0214720 A1 | * | 9/2005 | Milanovich et al. | 433/215 |
| 2006/0099155 A1 | * | 5/2006 | MacDonald et al. | 424/53 |

OTHER PUBLICATIONS

H.A. Bewick and J.K. Farrell, "Hydrogen Peroxide", in ETC 1st ed., vol. 7, vol. 13 and online by Wayne t. Hess, E.I.du Pont de Nemours & Co., Inc., Dec. 4, 2000.*

* cited by examiner

*Primary Examiner* — Walter Webb
(74) *Attorney, Agent, or Firm* — Peter B. Scull; Hamilton, DeSanctis & Cha LLP (57) ABSTRACT

An effervescent foamable two-component oral care composition in which a first component contains an acid, and a second component contains an alkaline source such as a carbonate; wherein one or both of the first and second components also contains a surfactant; and, wherein the first and second components are combinable to form an effervescing oral care foam.

20 Claims, 4 Drawing Sheets

FOAMING COMPOSITIONS AND METHODS

CROSS-REFERENCE TO RELATED APPLICATIONS

The present invention claims the benefit of and priority from the prior-filed U.S. Provisional Patent Applications, No. 60/653,421; filed Feb. 15, 2005, entitled "Whitening System Capable of Delivering Effective Whitening Action"; and No. 60/734,549 filed Nov. 7, 2005, entitled "Oral Care Compositions and Methods"; the subject matter of each of which hereby being specifically incorporated herein by reference for all that they disclose and teach.

BACKGROUND

The present invention relates to improvements in oral care compositions, and more particularly relates to two component foaming oral compositions and methods for the use thereof. Foaming tooth whitening compositions and methods are particular examples hereof.

In the state of the art of oral care compositions and the delivery thereof to the site of use in the oral cavity, many means and methods have been utilized and yet numerous issues remain. For an effective ingredient of an oral care composition to have a therapeutic effect, whether for oral cleaning, treatment or tooth whitening, the effective ingredient must reach and be maintained in effective contact with the oral care feature long enough to provide its intended effect. Thus, dispersion and penetration into and between the surfaces of various oral features such as the odd shapes of the nooks and crannies of adjacent teeth is a continual issue. So too then is the dwell or contact time necessary or at least preferred for having the effective ingredient or ingredients of an oral care composition maintained in contact with or otherwise disposed adjacent the surface of the oral feature being cared for. Such issues arise in various oral cleaning, treatment and/or tooth whitening situations.

In tooth cleaning and/or treatment, effective ingredients such as fluoride or an anti-gingival agent, e.g., triclosan, must reach the areas between teeth or between a tooth and gums and/or reach the nooks and crannies on/of teeth to provide their benefits to those oral features.

Similar activities are necessary in tooth whitening as well. In considering tooth whitening generally, it may first be noted that a tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a pellicle film on the teeth. These staining and discoloring substances can then permeate the enamel layer. This problem occurs gradually over many years, but imparts a noticeable discoloration of the enamel of one's teeth.

There are available to dentists and consumers many different oral compositions for home and professional in-office use which contain 1-45% by weight concentrations of a peroxygen compound such as hydrogen peroxide and when applied on the teeth may effect whitening of stains. These compositions all require different amounts of time to achieve a desired tooth bleaching effect. These times range from 90 to 120 minutes for a dentist applied, light-activated bleaching system to two weeks or more of over night exposure for tray-delivered whitening products. Currently, even the top selling brands of dentist applied, light activated chair-side tooth whitening systems require a minimum of three (3) twenty-minute applications and an overall minimum of ninety (90) minutes or more to complete when all manufacturers' instructions have been followed.

Among the chemical strategies available for removing or destroying tooth stains, the most effective compositions contain an oxidizing agent, usually a peroxygen compound such as hydrogen peroxide, in order to attack the chromogen molecules in such a way as to render them colorless, water-soluble, or both. In one of the most popular approaches to whitening a patient's teeth, a dental professional will construct a custom-made tooth-bleaching tray for the patient from an impression made of the patient's dentition and prescribe the use of an oxidizing gel to be dispensed into the tooth-bleaching tray and worn intermittently over a period of time ranging from about 2 weeks to about 6 months, depending upon the severity of tooth staining. These oxidizing compositions, usually packaged in small plastic syringes, are dispensed directly by the patient, into the custom-made tooth-bleaching tray, held in place in the mouth for contact times of greater than about 60 minutes, and sometimes as long as 8 to 12 hours. The slow rate of bleaching is in large part the consequence of the very nature of formulations that are developed to maintain stability of the oxidizing composition.

Alternatively, there are oxidizing compositions (generally those with relatively high concentrations of oxidizers) which are applied directly to the tooth surface of a patient in a dental office setting under the supervision of a dentist or dental hygienist. Theoretically, such tooth whitening strategies have the advantage of yielding faster results and better overall patient satisfaction.

Oral compositions for whitening teeth have also been available containing peracetic acid dissolved or suspended in a vehicle. The peracetic acid may have been generated within a dentifrice vehicle by combining water, acetylsalicylic acid and a water soluble alkali metal percarbonate.

Formulations for oxygen liberating compositions for the whitening of teeth have also used either anhydrous and/or hydrated pastes or gels. Hydrated examples include an aqueous oral gel composition comprising about 0.5 to about 10% by weight urea peroxide and 0.01 to 2% by weight of a fluoride providing compound, and/or a water containing a hydrogen peroxide-Pluronic thickened oral gel composition.

Other examples include a toothpaste containing a combination of calcium peroxide and sodium perborate oxidizing agents, dicalcium phosphate, calcium carbonate and magnesium carbonate cleaning agents, sorbitol humectant, cornstarch and cellulose gum thickening agents, and an anionic detergent, and/or oral compositions containing peroxyacids and alkyl diperoxy acids having alkylene groups containing 5-11 carbon atoms for removing stains from teeth.

Yet another conventional example includes administering a light-activated gel under the supervision of a dentist using a protocol of a usual three (3) twenty minute applications. Patients frequently become uncomfortable, agitated and/or bored during such a procedure that typically lasts 1.5 to 2 hours when all set-up and precautionary methods have been included. Also, because of the length of exposure to both the gel and the light, teeth and oral tissues can become irritated or experience a transient hypersensitivity reaction. Thus, any improvement that can result in decreased time, increased patient comfort and increase in bleaching efficiency is desirable.

More specific background information on activating bleaching agents with light energy includes the following. Scientists have identified many kinds of UV photoactivators, which are capable of working in nature to reduce the color of chromophoric stains. These include: transition metal complexes, keto acids, riboflavin, pteridines, algal pigments, cyanocobalamine, thiamin, biotin and aromatic ketones. The pathways by which photo beaching can theoretically occur on tooth surfaces are of two types. First, if the absorption spectrum of the colored chromagen overlaps with the spectrum of incoming radiation, the substrate may undergo photoreaction directly—e.g., the notion of fading color with light. Secondly, and likely a more powerful means for effecting color changes, UV energy may be absorbed by photo activators that then react with tooth surface chromagens, resulting in an "indirect" photobleaching.

Indirect photobleaching may be mediated by transient species (free radicals) that are rapidly consumed by subsequent reactions. For these mechanisms, the rate of reaction is determined by the quantity and type of chromagen, activator, free radicals and incoming UV radiation. Surface gradients involving any of these factors will lead to altered rates of photobleaching at the enamel/bleaching agent interface.

In nature, the major photochemical intermediate free radicals include singlet oxygen, $1O2$; superoxide $O2-$, hydroperoxide $HO2°$ and various other peroxy radicals, $RO2$. These have been described in more than one hundred patents for the purpose of bleaching teeth. Singlet oxygen free radicals (the most common type of free radical liberated from hydrogen peroxide in the presence of light, heat or most activators), $1O2$, are formed primarily through energy transfer from the excited triplet states of dioxygen, $3O2$ (as seen in the case of hydrogen peroxide), and wavelengths in the UV-A (315-400 nm) and UV-B (280-315 nm) have been shown to be most effective in their formation. Quantum yields (the fraction or percentage of absorbed photons which give rise to products) range from 1 to 3% and generally decrease with increasing wavelength. Because the high concentrations of hydrogen peroxide or similar compounds are present in tooth bleaching preparations, its decay into water and $1O2$ is dominated by this pathway when UV light/activator systems are used in professional tooth bleaching formulas.

The exact mechanism of how these singlet oxygen free radicals come to be formed still remains unclear. Some researchers have suggested that $1O2$ is formed by direct electron transfer from the excited triplet states to $O2$. However, reduction of $O2$ by radicals or radical ions produced by intramolecular electron transfer reactions, H-atom abstractions and/or homolytic bond cleavages, is equally, if not more plausible. However, it is known that transition metal complexes having one-electron reduction potentials falling between the $O2/O2-$ and $O2-/H2O2$ couples can rapidly catalyze $1O2$ free radical formation.

A commercial application has been made of oxidation from the photo-fenton reaction in which reduced metals such as Fe(II) react with $H2O2$ and UV light to produce a single OH— radical. This may be because hydroxyl moieties may be generated with less UV activation energy reduction in a chromophoric tooth stain in a given period of time or for a given level of UV energy (the high quantum yield for this reaction is 98%).

These extant methods are not quickly nor highly effective and indeed need prolonged periods for any minimum effective bleaching effects. These time-consuming methods thus suggest that any whitening system that can reduce the time factor is desirable.

SUMMARY

The present invention relates to two-component foaming oral care compositions. More particularly, herein described are two-component foamable compositions having a first component including at least one acid compound; and a second component including an alkaline source such as a carbonate. A surfactant may also be included in either one or both of the first and or second components. A peroxide may be added to the acid component to provide a tooth whitening composition. A potassium iodide or like substance may be added to the alkaline source component. A nitric acid may also be included in the acid component for coloring the composition. A potassium or like nitrate and/or a Eugenol component may be added to one or the other of first and/or second components as a desensitizing agent and/or for a viscosity contribution. Other additives may include calcium nitrate or the like and/or sodium mono and/or dibasic hydrate for contribution to viscosity or surface tension properties. Also, a light activator such as ferrous gluconate may be added to enhance peroxide whitening using light activation.

DETAILED DESCRIPTION OF THE DRAWINGS

DETAILED DESCRIPTION

The detailed description set forth herein is intended as a description of several of the presently exemplified oral care compositions provided hereby and is not intended to represent the only forms in which such compositions may be prepared or utilized. The description sets forth the features and the steps for preparing and using the oral care compositions hereof. It is to be understood, however, that the same or equivalent functions and ingredients incorporated in the oral care compositions may be accomplished by different embodiments that are also intended to be encompassed within the spirit and scope hereof.

As used herein, foaming and more particularly effervescent foaming refers to a growing foam, generally of substantially small, or otherwise substantially consistently-sized, orally-acceptable bubbles. An effervescent foaming composition hereof generally includes compositions which evolve gas by means of a chemical reaction between an acid and a base which takes place upon exposure of the acid and the base to each other. Thus, the acid and base are maintained separate (even if but merely in separate phases in a common compartment) until use when the separate components are brought into contact with each other to create a foaming oral care composition.

Each of the acid and/or the base may also be disposed in or otherwise be brought into contact with water or other fluids. Liquid forms of the respective components may provide stability and decrease viscosity, lower viscosities contributing to enhanced dispersion and penetration. Moreover, the effervescence and/or foaming is here generally used to also enhance dispersion as well as increase dwell time in the oral cavity of the active ingredient(s) of the effervescent foaming oral care composition. Controlled and/or consistent bubble formation in an effervescent foam such as those herein can thus also contribute to better oral care, cleaning and in some embodiments, whitening of teeth. Gas eruption in the effervescent foaming hereof is orally-acceptable, and thus is typically slow and gentle, however, more explosive foaming may also be usable herein/herewith so long as such remains orally acceptable (e.g., not causing undesirable damage, as to any of the oral tissues or surfaces). Foaming agents hereof are thus those generally of a chemical nature, including chemical agents that aid in foam generation, as well as aiding in sustained foaming, generating a gas that produces foaming, or in assisting a composition to become self-effervescent, or an agent that produces similar results. Again, though generally of a chemical reaction nature herein, a foaming agent hereof may alternatively include in some implementations, a mechanical foaming initiator or contributor as well.

In a first group of embodiments, the compositions hereof may include two components; a first one of which containing an acid, and the second one of which containing a base, typically a carbonate. Either or both of these components may then also include a surfactant. Such a two-component composition may then provide an effervescent foam when the first and second components are brought into contact with each other. Indeed, no agitation or external gas need be added in many such embodiments. A surfactant such as pluronic F68 may be used to control bubble size; e.g., smaller bubbles. This may also provide for longer lasting bubbles/foams. Such a composition, when formed into a foam can be used to clean oral tissues or surfaces; in one example, such may form a denture cleanser. In many embodiments, these first and second components are liquids which enhance stability and reduce viscosity.

A foamable composition such as those hereof is thus preferably manageable during use, is preferably capable of delivering a high concentration of oral care or cleaning compounds without confinement problems. The foamed composition can also seek to fill crevices and gaps (nooks and crannies) between teeth or other tissue surfaces. Foam also has the ability to drain into and seep into gaps where gaps are not apparent, thus offering effective whitening action, or other oral care activity, not only to the front surface of a tooth, but surfaces between teeth as well. Contrarily, previous viscous compositions could not flow between the surfaces, and thickeners inhibited the availability of oral care compounds from reaching the intended surfaces.

Aqueous solutions and gels without foaming action or surfactants tend to hold drops of water together as they try to become spherical, which is the reason why water tends to flow in tendrils rather than in sheets. At the atomic level, surface tension is seen as a macro effect of unbalanced electrical forces at the surface of the liquid, the same electrical forces that hold the molecules of the liquid together and keep it from evaporating. Within the body of a typical aqueous solution or gel, there are lots of molecules in all directions, and electrical forces are balanced on the average. A molecule is pulled equally in all directions by neighboring molecules, resulting in no net force thereon. On the surface, however, there are only a scant few air molecules to counteract the pull of the liquid below. The result is an inward-directed force pulling on a molecule near the surface, ultimately forming an electrical armor that envelops the liquid like an ultra thin skin. Thus, it is easy to see that non-foaming oral care gels tend to hold on to their active ingredients. Water molecules near the surface of gels intensify and magnify the surface tension, resulting in a so called "skin" effect by aligning to form a type of "elastic electrical force field" that seals and shields the surface even more. The shape of the water molecule leaves one of its ends with a slightly positive charge and the other end with slightly negative. Because of this electrical asymmetry (known as polarization), the negative and positive ends of adjacent molecules attract one another, creating a weak but significant physical bond. Energy is then required to stretch and break the bonds, and spreading out the liquid would mean that some of the bonds have to be broken. In this manner, most of the active oral care molecules in a typical oral gel have difficulty escaping from the surface tension bondage to perform their intended function.

Foams in general have lower surface tension than their liquid solution counterparts prior to foaming and can therefore be spread as thin as one molecule thick sheets, while at the same time increasing their respective surface areas. Thus, it is clear that foamable compositions hereof have advantages over gels and solutions. Without being bound to any particular theory, it is surmised that active oral care ingredients can be captured inside the bubbles of foams. As the bubbles collapse, the active agents may be released to perform oral care actions. Also, the foamed bubbles, through the forces of capillary action and lowered surface tension, are also wetting agents, an oral care solution can penetrate through smaller openings by weakening the electrically charged "skin of surface tension" typically found in aqueous solutions and gels. The rapid penetration into the tightest spots is also aided by the distribution of bubble sizes and shapes. Thus, foams can cause deeper penetration of active peroxide molecules. Additionally, foaming agents increase the adhesion of a liquid to a solid surface by allowing it to spread over a greater surface area.

It is further surmised that aside from the ability to lower surface tension, foams can also act to propel the active oral care molecules toward the teeth and also act as a molecular "Lint Roller" to grab stains or other undesirable features and lift them off of tooth surfaces.

Oral care compositions hereof may generally include a surfactant which may be a part of or define a foaming agent. Suitable surfactants may be anionic, nonionic, amphoteric, zwitterionic, cationic, and/or mixtures thereof. Some of these many kinds of surfactants aid in foam formation and some do not. Some surfactants are useful purely for their foaming properties alone, some act only as emulsifiers or wetting agents without foaming, and some may even act to reduce foaming. Herein, the surfactants may preferably though not necessarily include, for example, those that not only have foaming capabilities, but also those with the ability to act as wetting agents. Surfactants having either foaming or wetting abilities may also be used.

Anionic surfactants include, but are not limited to water-soluble salts of alkyl sulfates having from 8 to 20 carbon atoms in the alkyl radical (e.g., sodium alkyl sulfate), water-soluble salts of sulfonated monoglycerides of fatty acids having from 8 to 20 carbon atoms and mixtures thereof. Examples of anionic surfactants include sodium lauryl sulfate (SLS), sodium coconut monoglyceride sulfonates, phospholipids, sarcosinates, such as sodium lauryl sarcosinate, taurates, sodium lauryl sulfoacetate, sodium lauroyl isethionate, sodium laureth carboxylate, and sodium dodecyl benzenesulfonate. Many of these anionic surfactants are disclosed in U.S. Pat. No. 3,959,458, the content of which is incorporated herein in its entirety by reference.

Nonionic surfactants can include, but are not limited, to compounds including a hydrophilic and hydrophobic components (which may be produced by the condensation of alkylene oxide groups (hydrophilic in nature) with an organic hydrophobic compound which may be aliphatic or alkylaromatic in nature). Examples of suitable nonionic surfactants include low viscosity poloxamers (under trade name Pluronic), low viscosity hydroxyethyl cellulose, polysorbates, polyoxyethylene sorbitan esters (under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures thereof.

Amphoteric surfactants can include, but are not limited to derivatives of aliphatic secondary and tertiary amines in which the aliphatic component can be a straight chain or branched and one of the aliphatic substituents contains from about 8 to about 18 carbon atoms and one contains an anionic water-solubilizing group, e.g., carboxylate, sulfonate, sulfate, phosphate, phosphonate, betaines, specifically cocamidopropyl betaine, and mixtures thereof. Many of these nonionic and amphoteric surfactants are disclosed in U.S. Pat. No. 4,051,234, the content of which is incorporated herein by reference in its entirety.

Actually, any asymmetrical molecule dissolved in water will make at least a weak surfactant. Such weak surfactants may normally not be an effective foaming agent, but its effectiveness can be improved if an alternatively available foaming dispenser is also used. Asymmetrical molecules as used herein may include those that contain a hydrophilic (water-loving) and a hydrophobic (water-fearing) segment. One end of the molecule is thus polar in nature and dissolves in water, while the other end is nonpolar in nature, avoids water and dissolves in oil and other nonpolar compounds. When in water, surfactant molecules aim their polar ends at the water molecules, leaving the nonpolar ends sticking out like little electromagnets to attract nonpolar molecules. It is surmised that in a foamable composition such as those hereof, the polar ends may eject active oral care molecules like a rifle, and the non-polar ends lift tooth surface stain molecules like a chemical "lint roller" that loosens, breaks up and holds them onto the polar molecules, allowing them to be washed away with the water.

Either or both the first or second component in the two-component compositions hereof can also or alternatively include at least one surfactant in solid form. The ingredients in solid form, for example, can include Pluronic F68, Sodium Carbonate anhydrous, Sodium Bicarbonate, potassium iodide and mixtures thereof. For a further example, surfactants hereof may include at least some difunctional block copolymer surfactant, such as those having terminal groups of primary hydroxyl groups, as well as those comprising a hydrophobic and a hydrophilic segment. Examples include Pluronic F68, Pluronic F88 and mixtures thereof.

The amount of a surfactant used herein can range, for example, from about 0.1% to about 5% by weight of the foamable composition, or for a further example, the surfactant can range from about 0.5% to about 3% by weight, and for a still further example, the surfactant can be less than about 1% by weight.

Still other foaming agents can include reaction products of any effervescent compound with an acid. The effervescent compound, i.e., basic or alkaline source compound, is, for example, a pharmaceutically acceptable alkali metal carbonate or bicarbonate, such as sodium bicarbonate, potassium bicarbonate, sodium carbonate or potassium carbonate. The typical exemplar used in the below-presented examples is sodium bicarbonate. The amount used can range, for example, from about 1% to about 10% by weight, or, from about 3% to about 7% by weight, or still further, for example, from about 3.5 to about 5.5% by weight of the composition. The amount used depends on the volume of foam required, the desired pH and the desired diffusional or proper osmotic activity of the foam to be formed.

Examples of suitable acids include water soluble carboxylic acids such as nitric, citric, lactic, tartaric, succinic, glycolic, malonic, oxalic, malic, fumaric, maleic, or acetic acid, and phosphoric acids. A few of the examples include 85% phosphoric acid, citric acid or tartaric acid, in an amount of from, for example, about 0.5% to about 5%, or for a further example, from about 1% to about 3% by weight of the composition.

Generally, the ratio of acid and basic compound ranges from, for example, about 1:0.5 to about 1:25, or in a further example, from about 1:1 to about 1:4, by weight.

The first and/or second components may typically be liquids and will often include a carrier. Water ($H_2O$) is a common carrier. In many embodiments, these first and second components are both liquids which may enhance stability and reduce viscosity.

In another group of embodiments, compositions hereof may include at least one peroxide compound to create a tooth whitening composition (though it may remain an oral care cleanser as well, see above). The peroxide may be hydrogen peroxide or may be one or more of other peroxides such as those for example, which may include metal ion free peroxide compounds. Thus, examples of suitable metal ion free peroxide compounds include hydrogen peroxide and organic peroxides including urea peroxide (carbamide peroxide), salts of peroxides formed from the alkali and alkaline earth metals, glyceryl peroxide, benzoyl peroxide and the like. A few of the examples of the peroxide to be included in the first and/or second component are hydrogen peroxide or a mixture of hydrogen peroxide and carbamide peroxide. Others include calcium peroxide and/or mixtures thereof with either or both hydrogen and/or carbamide peroxide. The total peroxide present in the foamable oral care composition, may for example, range from about 1% by weight to about 45% by weight of the composition, further for another example from about 5% by weight to about 35% by weight of the composition.

When hydrogen peroxide is used, it is usually provided as an approximate 50% aqueous solution. When used alone, the amount of the hydrogen peroxide aqueous solution in the first component may range from, for example, about 2% to about 90% (about 1% to about 45% in the absence of water), or as a further example, the amount may range from about 10% to about 60% (about 5% to about 30% in the absence of water). On the other hand, when carbamide peroxide is used, it may often be used in combination with hydrogen peroxide, though it can be used alone. When used in combination, the carbamide peroxide may then generally be present in an amount from, for example, just slightly more than about 0% by weight to about 40% by weight, and, for a further example, in an amount from about 3% to about 35% by weight. Hydrogen peroxide, generally provided as an approximate 50% aqueous solution, may be present in an amount of from, for example, about 1% (w/w) to about 30% (w/w) (about 0.5% to about 15% in the absence of water); or for a further example, in an amount of about 5% (w/w) to about 30% (w/w) (about 2.5% to about 15% in the absence of water).

A peroxide such as those described above may be present in one or the other or both components of the composition.

Typically however, the peroxide will be in the acid containing component, the first component described above. Thus, the peroxide may be included in the first component in a range of from just above about 0% (w/w) to about 50% (w/w).

It has been understood that peroxides such as hydrogen peroxide, carbamide peroxide, and others such as salts of peroxides formed from the alkali and alkaline earth metals, readily attack and oxidize organic molecules. Known generally also is that such organic molecules are often involved in the stains in discolored teeth. Thus, there is some general understanding that peroxides are effective to oxidize and remove organic stains in/on teeth. Thus, when one or more peroxides are used, the oral care composition(s) may be tooth whitening compositions. Moreover, it is also understood that in certain circumstances, such oxidizing activity can be accelerated by the addition of heat, light and/or chemicals, particularly chemicals that can raise the pH of the peroxide environment. A dissertation of the possible mechanisms is presented in U.S. Pat. No. 6,116,900, "Binary Energizer and Peroxide Delivery System for Dental Bleaching" the teachings of which being hereby incorporated herein by reference.

In addition to the alternative addition of heat, light and/or chemicals, the amount of whitening obtained during tooth bleaching with peroxide compositions has previously generally been dependent upon (1) the length of time the teeth are in contact with the whitening agent; (2) the number and/or length of periods (e.g., hours and/or days) the treatment is carried out; (3) the susceptibility of the teeth to the bleaching agent; and (4) the concentration of active peroxide, as noted above. For maximum whitening, a long treatment time with a highly concentrated bleaching composition had generally been recommended.

Bleaching activity of a peroxide compound has generally been dictated by the availability of active peroxides. When peroxide is present in solution, active peroxides are readily available. However, a solution, by its nature, is not easily contained, and/or not amenable for sustain action when applied to a patient's teeth, again because it is difficult to confine it to any desired location. Thus, a less concentrated peroxide solution requiring longer contact time to be effective is not practical, while a more concentrated solution of peroxide, though more efficient in bleaching, still does not solve the confinement problem, and any concentrated solution coming into contact with soft tissue inside a patient's mouth can potentially cause tissue damage. Therefore, to maintain effective bleaching without potential tissue damage, various gelling agents, thickeners and adhesion promoters have been used to form pastes, gels, and similar forms to achieve prolonged contact effects. Unfortunately, such additives used to achieve prolonged contact also help to decrease the bleaching activity of peroxides by inhibiting the availability of active peroxides. For example, bleaching gels usually contain thickeners derived from polymers of acrylic acid (carbomer), pyrrolidone analog thickeners, or others, all lead to diminishing the whitening capacity of peroxides through ionic and covalent interactions within the gel, and thus act against the desired effect of tooth whitening. High surface tension effects of such gels can inhibit the escape of the peroxide from the gel, thereby limiting the effectiveness of the peroxide for its intended purpose.

As described above, a foamable composition such as those hereof can, on the other hand, solve the problems encountered by gels and the like. A foamed composition is manageable during use, is capable of delivering high concentration of peroxide (or other oral care or cleaning compounds) without confinement problems, while at the same time will not seriously inhibit the availability of active peroxides. The foamed composition can also seek to fill crevices and gaps between enamel rods. Foam also has the ability to drain into and seep into gaps where gaps (nooks and crannies) are not apparent, thus offering effective whitening action not only to the front surface of a tooth, but surfaces in-between teeth as well. A viscous composition that cannot flow between the enamel rods, and thickeners that inhibit the availability of active peroxides for tooth whitening, the present invention provides all the benefits not currently available to other whitening systems.

Faster acting foams may be found when a potassium iodide is added to one or the other of the first and second components, typically the second component, here the basic component. This will provide a quick acting foam with rapid radicals. However, a potassium iodide will form a colorful foam, usually yellowish or brownish, thus, a counteracting weak nitric acid may also be added to counter the potassium iodide coloring. This nitric acid may be added to one or the other of the first and second components, usually to the first component, here the acidic component. Then, when mixed, the first and second components would form a white foam which may have better cosmetic appeal, particularly in oral care and even more particularly in tooth whitening.

Since the whitening activity results when active peroxide comes into contact with the tooth, the foams generated, for example, are not too long lasting, but have a substantive body so that the amount of liquid formed, i.e., the collapsing of the foam bubbles to release active peroxide can be controlled and balanced. Therefore, some implementations of preferred compositions hereof are not only foamable, but are also capable of producing longer lasting, collapsible foams.

Though not required, such foams may thus have half lives of, for example, from about 2 to 60 minutes, or for a further example, of at least about 5 to about 30 minutes. A foam having a half life of 5 minutes means that 50% of the bubbles would collapse to release the encapsulated whitening agent, or that the volume of the foam is reduced by 50% in about 5 minutes after formation, and 75% of all the bubbles are gone, or the volume of the foam is reduced by 75% in about 10 minutes. The collapse time or half lives of the foam depends on a number of factors. For example, the greater the amount of bubbles formed, the longer the collapse time. Also, the lower the viscosity of the stabilizer, the shorter the collapse time. The collapse time may also depend on the nature of the other additives to the composition, which have surface active properties e.g., surfactants or preservatives.

The longer lasting foams can, for example, be generated by including a foam stabilizer in the composition. The foam stabilizer is, for example, a hydrogel-like mixture of gum and water. For example, the viscosity of a solution thickened with the stabilizer remains substantially the same in a wide pH range and is relatively independent of ionic strength and the thickener can be, for example, xanthan gum, clear xanthan gum, hydroxyethyl cellulose having about 1000-5000 cps, or the like and/or mixtures thereof. The advantage of xanthan gum is that compositions containing it can have a low viscosity at high shear rates, and are thus relatively easy to pump, spray or spread. Xanthan gum also exhibits a high viscosity at low shear rates, thus preventing the composition from dripping or flowing into places where it is not wanted. Thus, in addition to good stabilization of foams, it also gives it the substantive body needed. Xanthan gum is also widely used in the food industry and thus is safe for consumption.

The stabilizer may be, for example, used in such concentrations that solutions or dispersions containing it in its pre-swelled form have viscosities as measured by Rotational Viscometer CSR-10a of within the range of, for example, less than about 50 cps, further for example, less than about 20 cps, still further for example, less than about 10 cps. The concentration of stabilizers can range, for example, from about 0.1 to about 10%, further for example, from about 0.5 to about 5%, still further for example, less than about 1% by weight of the composition. When xanthan gum is used, it is, for example, present from about 0.5 to about 2% by weight of the composition. When hydroxyethyl cellulose is present, it is, for example, ranging from about 0.5 to about 2% by weight of the composition.

Perhaps surprisingly, the acidic compounds mentioned above, including tartaric, citric, nitric or phosphoric acid, if present, can also act as suitable stabilizers. The amount of acidic compound stabilizers, for example, ranges from about 0.1% to about 2% by weight of the composition.

In some examples hereof, the time before 50% of the foam collapses is sufficiently long so that the teeth can be about 7 to about 8 shades lighter than their original tooth shade after three (3) applications of, for example, about 5 to about 10 minute duration when used in a photo-bleaching mode in a dental office setting. The advantage of the collapsibility of many foams formed by some compositions of the present invention is that they may collapse in a liquid of low viscosity, low surface tension and high ability to penetrate between teeth and between enamel rods, thus giving the bleaching composition the best opportunity to rapidly cause teeth whitening. On the other hand, the advantage of stable foams will insure that their adherence to teeth is better and thus will not running off or have to be constantly reapplied. Also a greater the volume of the foam, will provide a higher concentration of peroxide that can be used to cause rapid whitening of teeth without causing soft or hard tissue sensitivity issues. The ideal foam stability/collapsibility can also be easily adjusted according to customer desire.

For example, if present, any thickener will also preferably have a low viscosity so as not to inhibit the availability of active peroxides. The viscosity is generally, for example, less than about 5000 cps or perhaps less than about 1000 cps, or for a further example, less than about 500 cps, and further for example, less than about 100 cps and as fluid as less than 50 cps.

The composition of the present invention can also include other active ingredients, such as de-sensitizing agents and/or antimicrobial or anti-bacterial agents.

Even with improved efficiency and shorter treatment time, some patients may still experience sensitivity. Suitable desensitizing agents can include Eugenol and/or alkali nitrates such as potassium nitrate, sodium nitrate and lithium nitrate; and other potassium salts such as potassium chloride and potassium bicarbonate. A potassium nitrate and/or Eugenol may be the preferable agent used. The desensitizing agent may be disposed in either one or the other of the first and second components, typically in the first. The percent of desensitizing agent can be present up to about, for example, 5 percent by weight, further for example, up to about 4 percent by weight, and even further for example, up to about 3 percent by weight.

Antimicrobial or anti-bacterial agents may also be included, an example of which may be Eugenol. Eugenol may be included in either of the first and second components, typically in the first.

Further additives may include Calcium nitrate and/or Sodium mono and/or dibasic hydrate. These may be added to decrease surface tension and/or lower viscosity to provide a composition which is more "liquidy" and thus more able to get into the nooks and crannies. Stability may also be improved hereby. These additives may be added to either of the first and/or second components, typically the calcium nitrate into the first component and the sodium mono and/or dibasic hydrate into the second component. As mentioned above, potassium nitrate may alternatively and/or additionally be added for these surface tension and/or viscosity effects.

The composition of the present invention can also include other active ingredients, such as peroxide activators, re-mineralizing agents, and fluoridating agents.

The addition of peroxide activators can also increase the photobleaching efficiency of the foamable compositions of the present invention. Suitable peroxide activators may include those with lower oxidative state transition metal salt. The metal salt may catalyze the bleaching action of the peroxide to produce faster effective bleaching at lower peroxide concentrations. The preferred transition metals are those of lower atomic numbers including lower atomic number transition metals such as those ranging from atomic number 21 to 30. Also, those with lower oxidative states may be more preferred, including, e.g., Iron(II), manganese(II), cobalt(II), copper(II) and mixtures thereof, and most preferably Iron(II), as in a ferrous gluconate. These may be added into either of the first and second components, typically in the second component. When used, only a very small amount of the transition metal salt is needed, for example, from about 0.01% by weight to about 4% by weight, further for example, from about 0.03% by weight to about 2% by weight, and even further for example, from about 0.04% to about 1% by weight. The peroxide activator can also include alkali salts such as potassium iodide, potassium chloride, sodium iodine, sodium chloride and combinations thereof.

Amorphous calcium compounds such as amorphous calcium phosphate (ACP), amorphous calcium phosphate fluoride (ACPF) and amorphous calcium carbonate phosphate (ACCP) amorphous calcium carbonate phosphate (ACCP), and amorphous calcium carbonate phosphate fluoride (ACCPF) can be used for remineralizing teeth. These amorphous compounds are disclosed in U.S. Pat. Nos. 5,037,639, 5,268, 167, 5,437,857, 5,562,895, 6,000,341, and 6,056,930, the disclosures of each of which hereby being incorporated by reference in their entireties.

In addition to or as an alternative to amorphous calcium compounds, amorphous strontium compounds such as amorphous strontium phosphate (ASP), amorphous strontium phosphate fluoride (ASPF), amorphous strontium calcium phosphate (ASCP), amorphous strontium calcium carbonate phosphate (ASCCP), amorphous strontium carbonate phosphate fluoride (ASCPF) and amorphous strontium calcium carbonate phosphate fluoride (ASCCPF) may be included for use in re-mineralization, as noted above. Such compounds are disclosed in U.S. Pat. No. 5,534,244, the content of which hereby incorporated by reference in its entirety.

For example, the first component of the whitening system may include a source of phosphate and the second component may include a source of calcium or strontium. For example, the source of phosphate in the first component may include monosodium phosphate ($NAH_2PO_4$), disodium phosphate, tetrapotassium pyrophosphate and/or mixtures thereof. As discussed above, the second component, for example, may include a source of calcium or strontium, which, when the two gel components are mixed, may combine with phosphate to form the various amorphous calcium and/or strontium phosphates. The source of phosphate may be, for example, present in an amount of from about 0.2% to about 5% by weight, further for example, between about 0.2% to about 4% by weight. The source of calcium, strontium or combinations thereof in the second component, for example, may include a calcium salt, a strontium salt, and thereof, further for example, a calcium salt such as calcium nitrate, in an amount of from about 0.25% by weight to about 1.5% by weight, for example, about 0.3% to about 1% by weight.

When the two components are mixed, the source of phosphate and the source of calcium, strontium or mixture can combine to form calcium phosphate. When applied to the teeth, the calcium phosphate can precipitate onto the surface of the teeth where it may be incorporated into hydroxyapatite, assisting in remineralization of the tooth enamel, as discussed in U.S. Pat. Nos. 5,037,639; 5,268,167; 5,460,803; 5,534,244; 5,562,895; 6,000,341; and 6,056,930 noted above.

In practice, it may in some embodiments be preferred to include as much phosphate as possible, as the phosphate salt may further act to adjust the pH of the first component. The pH of the system is from, for example, about 5 to about 8, further for example, particularly for the first component, from about 5.5 to about 6.5.

Note also, the fluoride-containing amorphous compounds described here may also be used in fluoridating teeth. Otherwise, as mentioned, fluorides may be added separately and then, many, if not all of the above amorphous compounds or solutions which form the amorphous compounds, when applied either onto or into dental tissue, particularly in the presence of fluoride, may operate to promote fluoridation. Such fluoridation or other mineralization may serve to assist in prevention and/or repair of dental weaknesses such as dental caries, exposed roots and dentin sensitivity.

In addition, optional additives including emulsifiers, flavorings, coloring agents, anti-plaque agents, anti-staining compounds, excipients such as emollients, preservatives, other types of stabilizers such as antioxidants, chelating agents, tonicity modifiers (e.g. sodium chloride, manitol, sorbitol or glucose), spreading agents, pH adjusting agents and water soluble lubricants, e.g. propylene glycol, glycerol or polyethylene glycol. The concentration of each may easily be determined by a person skilled in the art. Lecithin, a natural emulsifier found in soy and other plants, and gum arabic, which comes from the sap of certain species of acacia trees, can be added for use as an emulsifier, dispersant and/or wetting agent herein. Suitable preservatives may include benzalkonium chloride, parabens, chlorhexidine acetate, chlorhexidine gluconate, sorbic acid, potassium sorbitol, chlorbutanol and phenoxyethanol. Suitable emollients are those used for topical applications, as for example, di-n-octyl ether, fatty alcohol polyalkylene glycol ether, 2-ethylhexyl palmitate, and isopropyl fatty acid esters. An emollient, if used, may preferably be dispersed in the same part as the stabilizer, if used.

For increasing peroxide stability during storage, a 3% disodium EDTA may be added to the component containing the peroxide. Alternatively, stability may be enhanced by storing the product in a dark, cool, dry place or refrigerated. The acidic mixture of a peroxide, when used, in the first component containing the acid may also/alternatively stabilize or provide a tendency to stabilize the peroxide.

In packaging the oral care composition(s) hereof, any convenient means for effecting or maintaining the separation of the two components before use can be utilized. Note, this may include the alternative of encapsulating of the components in a unitary compartment, multi-phase environment. In an initial example, a single container can be compartmentalized so that the two components are housed in separate physical compartments and may be dispensed simultaneously and admixed prior to application on the teeth or otherwise in the oral cavity. The mixture may occur in or at the tip of a nozzle or a two-opening configuration may be provided where the components are not mixed until application. The containers may also include static mixers. Alternatively, the two components can be contained in separate containers from which the respective phases are dispensed for admixture just prior to use. Exemplary packaging alternatives are disclosed in U.S. Pat. Nos. 5,819,988, 6,065,645, 6,394,314, 6,564,972 and 6,698,622, the subject matter of which being incorporated herein by reference.

In one exemplary embodiment of the present invention, the two components are provided in separate chambers of a dual-barrel syringe. Immediately before use, the two components are mixed together in, for example in several embodiments, about a 1:2 to about a 5:1 ratio (first component to second component) by actuating the syringe, further for example, the fluids are mixed in the 1:1 ratio. The admixed oral care composition may be applied to the surface of the teeth or other oral tissue surface directly from the syringe. Other combinations of the components are contemplated by the present invention, depending on the percentage (%) variation of ingredients present in each component.

Figure 1:
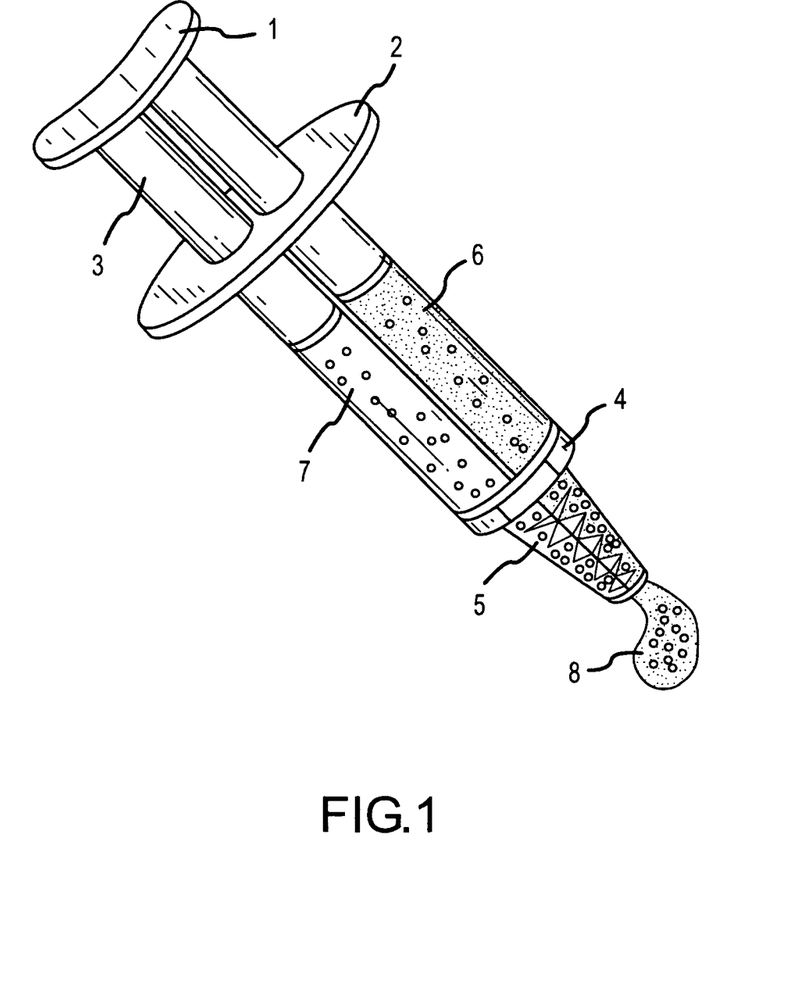
FIG. 1 is a dual-chamber syringe useful for dispensing compositions hereof.

FIG. 1 shows a possible embodiment of a delivery system suited for dispensing the present invention. It is a dual-component syringe, preferably constructed of polypropylene and comprised of a plunger 1, dual-barrel body with integrated finger rest 2, and pistons 3. A mixing syringe tip comprised of a locking outer housing 4 and integrated static mixer 5 is attached. Two complimentary oral care compositions 6 and 7 can be contained within each isolated syringe barrel. When the user is ready to use the invention, the plunger is actuated towards the direction of the tip, resulting in the compositions becoming admixed within the syringe tip/static mixer component. The resultant homogenous foaming whitener 8 is expressed out of the dispenser and is ready for use.

Figure 2:
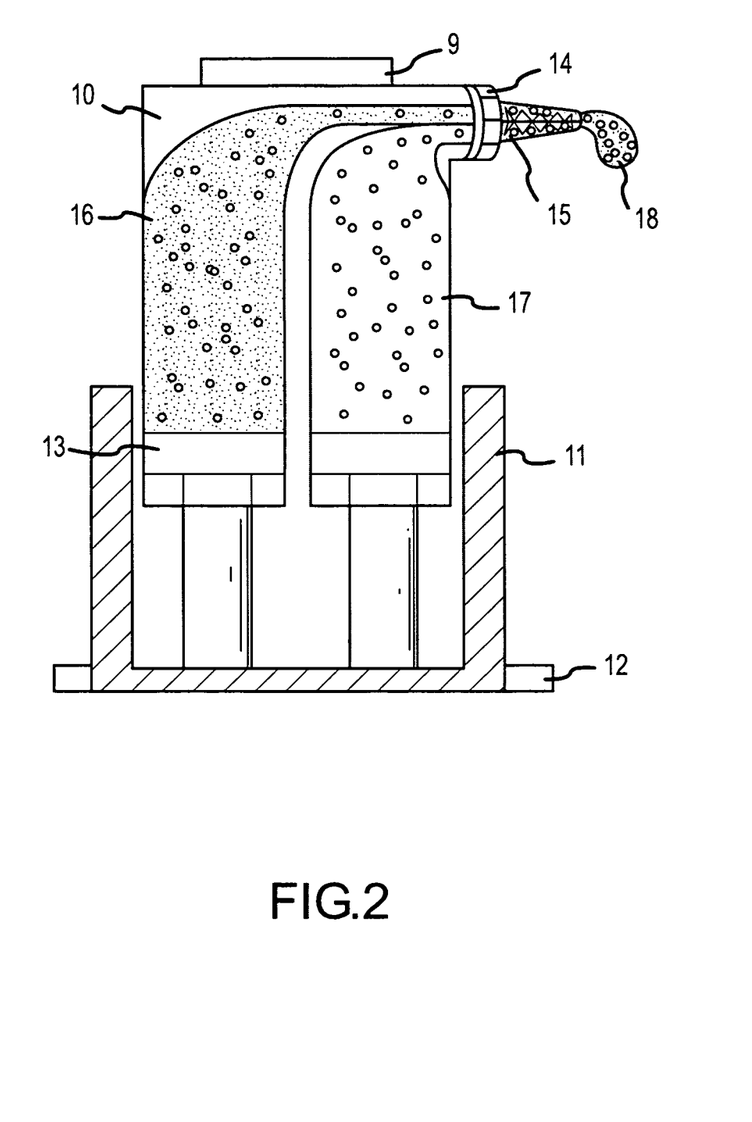
FIG. 2 is a dual-chamber dispenser useful for dispensing compositions hereof.

FIG. 2 shows a possible embodiment of a delivery system suited for dispensing the present invention. It is a dual-component dispenser pump, preferably constructed of high density polypropylene and comprised of a plunger 9, upper housing with dual-barrel inner holding chambers 10, and fit into a lower housing 11 and base 12. Air-tight septum closures 13 keep the whitening composition within the holding chambers and are displaced upwards by a vacuum created when the plunger 9 is actuated. Two complimentary oral care compositions 16 and 17 can be contained within each of the isolated holding chambers 10. When the user is ready to use the invention, the plunger 9 is actuated downwards, resulting in the compositions becoming admixed within the locking mixing tip complex 14 comprising a static mixer component 15. The resultant homogenous foaming composition 18 is expressed out of the dispenser and is ready for use.

Figure 3:
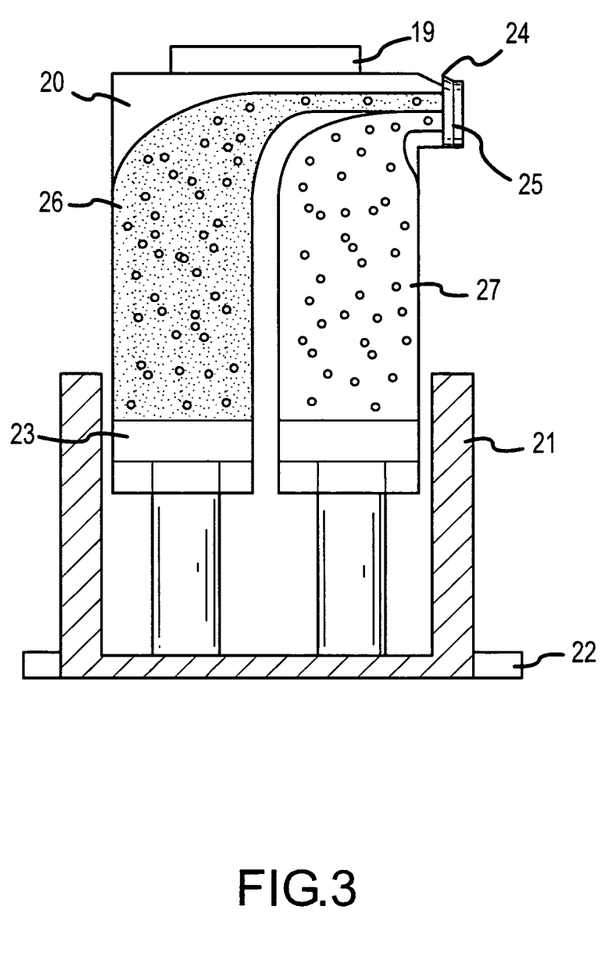
FIG. 3 is another dual-chamber dispenser useful for dispensing compositions hereof.

FIG. 3 shows a possible embodiment of a delivery system suited for dispensing the present invention. It is a dual-component dispenser pump, preferably constructed of high density polypropylene and comprised of a plunger 19, upper housing with dual-barrel inner holding chambers 20, and fit into a lower housing 21 and base 22. Air-tight septum closures 23 keep the whitening composition within the holding chambers and are displaced upwards by a vacuum created when the plunger 19 is actuated. Two complimentary oral care compositions 26 and 27 can be contained within each of the isolated holding chambers 20. When the user is ready to use the invention, the plunger 19 is actuated downwards, resulting in the compositions becoming expressed out of the dispenser from separate orifices. Two adjacent ribbons of the composition can be mixed together with a paint brush or swab, causing rapid foaming of the mixture. The foam can then be applied onto teeth. For storage of any remaining product, the pump has an integrated flip top closure 25 attached to the body with hinge 24.

In addition, any of the dispensers can also be fitted with a metering device for varying the proportion of each component in the final foam. The metering device can be adjusted to produce ratios of the two components from about 10:1 to about 1:10. The device can be in the form of a dispensing system which features a measuring mechanism that connects to two separate, interlockable bottles or like containers. By rotating the dispenser head, a precise mixing ratio of blended ingredients may be attained. In one specific embodiment, a dispenser head may include two pumps that offer varying proportions of volumetric dispensing that can be individually actuated in precise relationship to the positioning of an interior disc. This interior disc can be positioned precisely or locked into a specific ratio by rotating the dispenser head. The nozzle for metering dual dispenser pump bottle can either be a configuration in which both components are mixed with a static mixer incorporated within the tip thereof or a two-opening configuration where the components are not mixed until application. The use of metering devices can result in improved manufacturing efficiency, as fewer concentrations need to be made and the final concentration can be easily adjusted.

As noted above, the composition hereof may also be a multi-phase, foamable composition contained within a single unitary compartment, the composition including at least one acid compound in an aqueous phase and at least one basic compound in an oil phase. It is a well-known phenomenon that oil and water in general do not mix, and it is also a well-known phenomenon that they can be made to mix with the aid of foaming surfactants. Thus, upon mixing, the two-phases can combine to form a long-lasting, collapsible foam according hereto. When a preferred surfactant is used, the surfactant emulsifies and disperses the liquid by lowering the surface tension of both oil and water in order to effectively mix them together. Examples of solid surfactants are also difunctional block copolymer surfactants, similar to those listed above, including those having terminal groups of primary hydroxyl groups, as well as those comprising a hydrophobic and a hydrophilic segment. Examples include Pluronic F68, Pluronic F88 and mixtures thereof, inter alia.

As introduced above, substantivity, i.e. the ability of a product to linger, is a desirable property in any whitening or other oral care composition. On the other hand, when the desired property of a product is the ability to be rinsed off easily, a foaming surfactant may not be preferred in use. However, there is a desire in a whitening composition for both substantivity and the ability to be rinsed off easily. When this is desired, foams generated in a "foaming pump" can be used. Foaming pumps, as introduced above, can produce foams with all the desirable properties, while using a minimum of amount of surfactants, for example, of less than about 1.0%.

Alternatively and/or additionally, though not necessarily, a foaming agent can also be a gaseous material. The gaseous material can be any inert gas or the gas can be generated by mixing a basic solution with an acid solution comprising a potassium salt such as potassium bromide or potassium chloride.

The compositions and/or methods hereof are further described by the following examples:

Example 1

Ingredients for making an exemplary composition according to the present invention are set out in Table 1 below. They may be prepared as follows.

Component 1 (acidic) may be prepared by dissolving 0.8 grams of Pluronic F68 in 10 ml of water, followed by the addition of 0.5 grams of Potassium Hydroxide and 0.8 grams detergent with stirring using a lab mixer at room temperature. Then the mixture may be acidified by adding 3 milliliters of 10% nitric acid and 3 grams of tartaric acid w/stirring, at 500 rpm at room temperature. The entire solution may be diluted to 100 ml by adding 80 milliliters of a 50% Superoxol solution (50% hydrogen peroxide), followed by addition of 1 gram of Potassium Nitrate and stirred until thinned to a creamy white color. Next, 1.5 grams of Eugenol may then be added as an antibacterial agent, 2.0 milliliters of mint flavoring may be added to give a pleasant smell, and 0.5 grams of Calcium Nitrate may also be added. The mixture pH may then be checked. A pH range of about 1.5 to about 2.5 may be obtained through adjusting with either a 10% nitric acid or potassium hydroxide. The entire mixture may be agitated at room temperature under vacuum for 30 minutes. The resulting acidic low-viscosity solution (about 30 cps) may be poured into one of the 50 ml compartments of a two-chamber metering pump dispenser.

Component 2 (basic) may be prepared by adding 0.10 grams of potassium hydroxide and 0.50 grams of potassium iodide to 50 milliliters of distilled water, followed by the addition of 0.8 grams of detergent and 0.8 grams of foam stabilizer with stirring using a stand mixer set at 750 rpm at room temperature until a homogenous light hydrogel may be formed. Then 38 milliliters of 1% Calcium Peroxide suspension and 2 milliliters of glycerin may be added and blended until the mixture thins and appears clear and smooth. Then, 2 grams of sodium carbonate may be slowly added, followed by slow addition of 3 grams of sodium phosphate dihydrate, 1 gram of sodium bicarbonate and 0.10 grams of Disodium Phosphate. For photo activation purposes, if desired, 1.25 milliliters of 3.33% ferrous gluconate solution may be added while mixing at 200 rpm and then at 500 rpm. For aesthetic purposes, 1 ml of FD&C Green #2 may also be added. The pH may then be checked and adjusted with Potassium Hydroxide to a pH range of about 10.2 to about 11.2. Finally more distilled water may be added to bring the entire solution to 100 ml. To disperse and hydrate the stabilizer, and to degas any bubble(s) formed, this component may be agitated at room temperature under vacuum for 20 minutes. The resulting low viscosity solution (48 cps) may be poured into the other 50 ml chamber of the metering pump dispenser.

TABLE 1

| | | | | |
|---|---|---|---|---|
| Component 1 | | | | |
| Ingredient | Amount | Chemical/IUPAC "real" name | Available from | Purpose |
| H2O | 9.00 mL | Same | N/A | carrier/solvent |
| PLURONIC F68 | 0.80 g | Poloxamer 188 | BASF | Foamer |
| KOH | 0.50 g | Same | Spectrum Chemical | pH modifier |
| TYLOSE H4000* | 0.80 g | Hydroxyethyl cellulose | Clariant | Thickener |
| HNO3 10% | 3.00 mL | Same | Spectrum Chemical | pH modifier |

TABLE 1-continued

| | | | | |
|---|---|---|---|---|
| Tartaric Acid | 1.0 g | Same | Spectrum Chemical | foam stabilizer |
| 50% H2O2 | 80.00 mL | Same | Atofina | peroxide source |
| KNO3 | 1.00 g | Same | Spectrum Chemical | stabilizer - sensitivity reliever |
| EUGENOL | 1.50 mL | Same | Junbunzlauer | stabilizer - sensitivity reliever |
| MINT | 2.00 mL | Distilled peppermint oil | S&S Flavors | flavor, scent and stabilizer |
| $CaNO_3 \cdot (H_2O)_4$ | 0.50 g | Same | Spectrum Chemical | Calcium source |
| ethanol | 1.50 mL | Same | Spectrum Chemical | Solvent |
| KOH/HNO3 | QS to pH 2.0 | Same | Spectrum Chemical | pH modifier |

Component 2

| Ingredient | AMT | Chemical/IUPAC/ "real" name | Available From | Purpose |
|---|---|---|---|---|
| H2O | 50.00 mL | Same | N/A | carrier/solvent |
| KI | 0.50 g | Same | Spectrum Chemical | peroxide activator |
| KOH | 0.10 g | Same | Spectrum Chemical | pH modifier |
| PLURONIC F68 | 0.80 g | Poloxamer 188 | BASF | Foamer |
| TYLOSE H4000* | 0.80 g | Hydroxyethyl cellulose | Clariant | Thickener |
| 1% CaO2 Suspension | 40.00 mL | calcium peroxide suspended in H2O | Spectrum Chemical | peroxide source |
| Glycerin | 2.00 mL | Same | Spectrum Chemical | humectant, carrier, viscosity modifier |
| Sodium Carbonate | 1.00 g | Same | Spectrum Chemical | effervescent component |
| Sodium Phosphate Dihydrate | 1.50 g | Same | Spectrum Chemical | pH buffer and phosphate source |
| Baking Soda | 2.00 g | Sodium bicarbonate | Spectrum Chemical | effervescent component |
| DiSodium Phosphate Monohydrate | 0.50 g | Same | Spectrum Chemical | pH buffer and phosphate source |
| FeGluconate | 1.25 mL | ferrous gluconate | Spectrum Chemical | peroxide photoactivator |
| FDC Green #2 | 1.0 mL | FD&C Green No. 2 | Warner Jenkins | Colorant |

In one implementation, a 1:1 ratio may be used, such that substantially equal amounts of the first and second components are combined for use. In some implementations, a metering pump, such as those available from Versadial, Inc., of New York, N.Y., may be used. If so, the metering dial of some implementations of such a pump dispenser may be set so that 50% of each component may be dispensed simultaneously and mixed through a nozzle containing a static mixer into a 20 ml plastic weighed boat. The plunger may be actuated about 3-6 times, or more or less, for dispensing 5.0 milliliters into the weighed boat. Further mixing of both components may be made to occur by swirling the mixture for about 5 to about 10 seconds with a small disposable dental nylon applicator brush within the plastic well. The foam produced may be poured into a measuring cylinder. The volume of the expanded foam may be measured and its collapse with time monitored.

Figure 4:
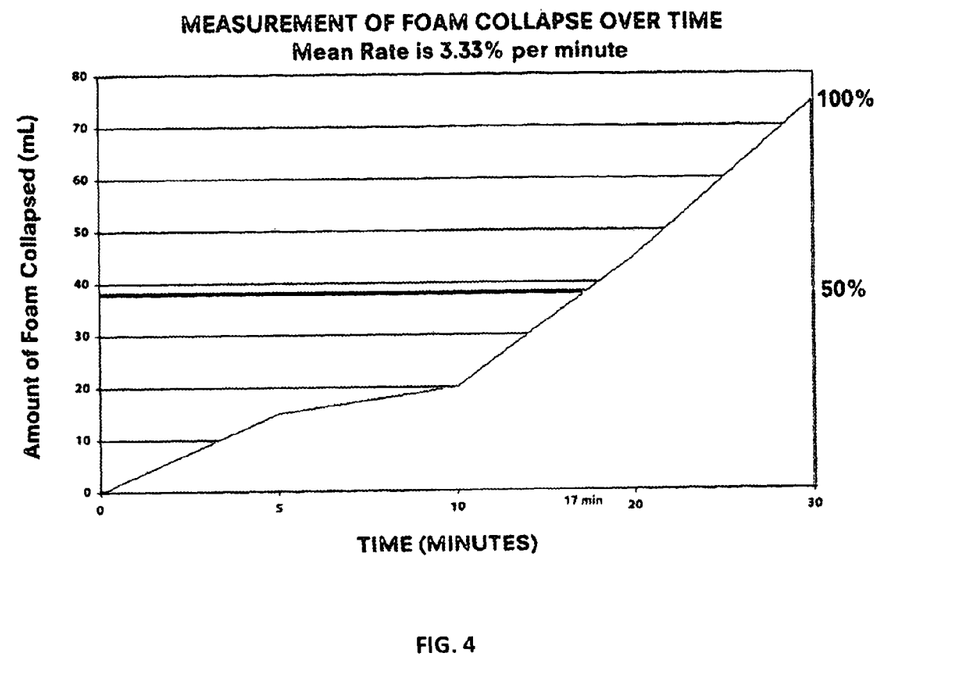
FIG. 4 is an illustration of a measurement of foam collapse over time.

Test results for this first example may be as follows. For the foam volume, collapse rate and pH; four (4) ml of each component may be used and it may take approximately 10 seconds to actuate the dispenser 10 times. A maximum volume of 75 ml may be obtained within about 3 minutes after the last discharge. After about 7 minutes, the volume may have decreased to about 35 ml, and after about 10 minutes the volume may decrease to about 20 ml. It may take about 30 minutes before the foam collapses completely. An example of collapse rate is s shown in FIG. 4 (found illustrated in the attached drawing sheet). The pH of the foam may be about 8.2. In another run, the amount of fluid used above may be about 3 ml from each chamber (about 6.0 ml total), and the total number of strokes of actuator may be about 6 (more or less). The volume expansion may then go from about 6 ml to about 75 ml.

Example 2

This second example composition may be made in a way similar to that of Example 1, except with different ingredients, as shown in Table 2.

TABLE 2

| Component 1 100 mL (acidic) | Component 2 100 mL (basic) |
|---|---|
| Water - 51 mL | Water - 93 mL |
| Tartaric Acid - 3.0 grams | Potassium Hydroxide - 0.7 grams |
| Sodium Lauryl Sulfate - 1 gram | Potassium Iodide - 0.9 grams |
| DiSodium EDTA - 4 grams | Sodium Lauryl Sulfate - 1.0 gram |
| Superoxol 50% $H_2O_2$ - 40 mL | Sodium Bicarbonate - 2.0 grams |
| Xanthan Gum - 1.0 gram | FD&C Blue #1 Solution 1 mL |
| Adjust pH with Citric or Tartaric Acid drop wise | Xanthan Gum - 1.0 gram |
| | Adjust pH with Potassium Hydroxide drop wise |

Both plungers of a dual chamber dispenser, if used here again, may be actuated at the same time to cause foaming. Mixing of components 1 and 2 may occur in the attached mixing tip. The foam produced may be filled into a measuring cylinder. The volume of the expanded foam may be measured and its collapse with time monitored.

The test experiment results for example 2 may be as follows. For the foam volume, foam collapse rate and pH; four (4) ml of each component may be used and it may take about 10 seconds to actuate the dispenser about 10 times. A volume of about 75 ml may be obtained about 5 seconds after the last discharge. After about 5 minutes the volume may decrease to about 60 ml, and after about 10 minutes the volume may decrease to about 55 ml. It may take about a half hour before the foam collapses completely. The pH of the foam may be about 6.78. Amount of fluid used may be about: 4 ml from each chamber (about 8.0 ml total); Number of Strokes of Actuator: about 10; Volume expansion: about 8 ml to (→) about 75 ml; Expansion multiple: about 9.4×.

Example 3

Example 3 may be made in the same manner as Example 1, except with different ingredients, as shown in Table 3 below:

TABLE 3

| Component 1 | | | | |
|---|---|---|---|---|
| Ingredient | Amount | Chemical/ IUPAC "real" name | Available from | Purpose |
| H2O | 9.00 mL | Same | N/A | carrier/ solvent |
| PLURONIC F68 | 0.80 g | poloxamer 188 | BASF | Foamer |
| TYLOSE H4000* | 0.80 g | Hydroxyethyl cellulose | Clariant | Thickener |
| 50% H2O2 | 80.00 mL | Same | Atofina | peroxide source |
| KOH/HNO3 | QS to pH 2.0 | Same | Spectrum Chemical | pH modifier |

| Component 2 | | | | |
|---|---|---|---|---|
| Ingredient | Amount | Chemical/ IUPAC/ "real" name | Available From | Purpose |
| H2O | 50.00 mL | Same | N/A | carrier/ solvent |
| KOH | 0.10 g | Same | Spectrum Chemical | pH modifier |
| PLURONIC F68 | 0.80 g | poloxamer 188 | BASF | Foamer |
| TYLOSE H4000* | 0.80 g | Hydroxyethyl cellulose | Clariant | Thickener |
| 1% CaO2 Suspension | 40.00 mL | calcium peroxide suspended in water | Spectrum Chemical | peroxide source |
| Sodium Carbonate | 1.00 g | Same | Spectrum Chemical | effervescent component |
| Baking Soda | 2.00 g | sodium bicarbonate | Spectrum Chemical | effervescent component |

Example 4

Example 4 may be made in a similar manner as Example 1, except for the different ingredients, as shown in Table 4 below:

TABLE 4

| Component 1 | | | | |
|---|---|---|---|---|
| Ingredient | Amount | Chemical/ IUPAC "real" name | Available from | Purpose |
| H2O | 9.00 mL | Same | N/A | carrier/ solvent |
| PLURONIC F68 | 0.80 g | poloxamer 188 | BASF | Foamer |
| 50% H2O2 | 80.00 mL | Same | Atofina | peroxide source |
| KOH/HNO3 | QS to pH 2.0 | Same | Spectrum Chemical | pH modifier |

TABLE 4-continued

| Component 2 | | | | |
|---|---|---|---|---|
| Ingredient | Amount | Chemical/ IUPAC/ "real" name | Available From | Purpose |
| H2O | 50.00 mL | Same | N/A | carrier/ solvent |
| KOH | 0.10 g | Same | Spectrum Chemical | pH modifier |
| PLURONIC F68 | 0.80 g | poloxamer 188 | BASF | Foamer |
| Sodium Carbonate | 1.00 g | Same | Spectrum Chemical | effervescent component |
| Baking Soda | 2.00 g | sodium bicarbonate | Spectrum Chemical | effervescent component |

Thus described are one or more two-component foamable composition(s) including a first component comprising at least one acid compound; and a second component comprising at least one alkaline source such as a carbonate, a carbonate providing a particularly desirable effervescing quality. A surfactant may also be preferably included in one or the other or both components. Each of the components may be in an aqueous solution or otherwise in liquid form, though other phases are also usable herewith. Compositions hereof may also be multi-phase, foamable compositions with at least one acid in a liquid phase, usually aqueous and a carbonate or other alkaline source in an oil phase. Other embodiments may include at least one peroxide compound in a first component, often in an aqueous phase and at least one carbonate in a second component, the carbonate may be a foaming agent in such an example. Still further, other compositions may include a foamable one or two-component composition comprising at least one peroxide compound, wherein the resultant foam has a half life of from about 2 to about 60 minutes. Furthermore, a composition hereof may include a two-component foamable composition having a first component comprising at least one peroxide compound in an aqueous solution and at least one peroxide stabilizer in the form of an ion scavenger; and a second component comprising at least one foaming agent and at least one peroxide activator; wherein said activator promotes the rapid decomposition of the peroxide compound and additional foaming action not related to the foaming agent. Additionally, another embodiment may include a light-activatable, two-component foamable composition having a first component comprising at least one peroxide compound; and a second component comprising at least one foaming agent and one lower oxidative state transition metal salt.

In some aspects, the foamable composition may be substantially free of gelling agents, thickeners, carbons, polymers and/or other ingredients that may tend to inhibit foaming. In yet a further aspect, the first component of the foamable composition may also include a de-sensitizing agent. In yet an additional aspect of the invention, the foamable composition may include at least one peroxide activator. In yet an additional aspect of the invention, the two-component foamable composition may contain peroxide compounds in both components. In yet an additional aspect of the invention, the foamable composition may include foam stabilizers. In yet an additional aspect of the invention, the foamable composition may include at least one solvent suitable for solubilizing stains. In a further aspect, the first component of the foamable composition may include at least one source of calcium, strontium and mixtures thereof and the second component may include at least one source of phosphate.

In still yet another aspect of the invention, the two-component foamable composition may be provided in a double-barrel syringe. In still yet a further aspect of the invention, the two-component foamable composition may be provided in a double-barrel pumpable dispenser. The pumpable dispenser can be provided with a metering device for varying the proportion of each component in the final foam. The metering device may be adjusted to produce ratios of the two components of about 10:1 to 1:10.

In another aspect, the foamable composition may include ingredients capable of increasing the half life of the foam that is generated. The stabilizer may, for example, be added to facilitate the formation of a water-soluble, longer-lasting, collapsible foam structure.

A method of use hereof may include using the oral care composition in a multi-component system including one or more of a two-, three- or four-component system, wherein the multi-component system includes one or more of an enhancer composition, one or more foaming components and a finishing composition.

In a further alternative, other organic or human tissue may be conditioned using compositions hereof. For example, melanin is an organic carbon-bonded molecule and is subject to whitening in much the same manner as organic tooth stain molecules. Darker skin pigmentation is caused by the over expression or accumulation of melanin in the skin. As a result, the application of an activated mild whitener composition, containing an oxidizing agent will work to make the skin appear whiter on a temporary basis. The resultant whitening is temporary as the epithelium and melanin are replaced on a daily basis. However to the extent that persons may want an instant temporary method of appearing cosmetically lighter, this method is one possible solution. The ability to modify the appearance of pigment content in the skin, to promote an even-looking skin tone and a more youthful appearance, is highly desired in many of the world's societies. Many people desire to modify their skin tone, to reduce aging spots, melasma, etc., or for purely cosmetic reasons. In fact, in the Far East, a lighter skin tone is desirable and is associated with higher socioeconomic status.

Therefore, the present invention, in an alternate embodiment may be used as a skin whitening composition which can be effectively used as a topical agent and which would cause rapid skin lightening. For this application, the preferred peroxygen would be benzoyl peroxide, and all other oxidizers, such as nitrogen oxide or sodium chlorite present should be preferably reduced by 50% or more in the overall composition. Furthermore, the composition of the invention described herein can be optionally combined with tyrosinase inhibitors, and/or melanin cell synthesis inhibitors, along with skin exfoliating agents, which are all useful in topically applied cosmetic skin whitening formulations described in the current art.

Having described the invention with reference to accompanying illustrations and examples of the invention, it is contemplated that other changes can be made without departing from the spirit or scope of the invention as set forth in the appended claims.

What is claimed is:

1. An effective amount of non-agitated effervescent oral care foam, the foam comprising:
   a non-agitated combination of a first component containing an acid; and
   a second component containing an alkaline source of equal to or less than about 2%;
   wherein one or both of the first and second components also contains a surfactant and a foam stabilizer to thicken the component, the foam stabilizer including at least the thickener hydroxyethyl cellulose and the foam stabilizer also optionally including one or more low viscosity thickeners and mixtures thereof to assist in maintaining the foam half-life;
   wherein the first and second components are structurally disposed to be combined and spontaneously form a substantial, non-agitated effective amount of effervescing oral care foam chemically outside the mouth with a half-life of foam of at least about 5 minutes and up to about 17-20 minutes without any mechanical mixing or agitation added, the effective amount being that amount to provide the give said half-life;
   wherein said first component further comprises at least one peroxide compound in an aqueous solution and at least one peroxide stabilizer in the form of an ion scavenger;
   said second component comprises at least one foaming agent and at least one peroxide activator, wherein said activator is disposed to promote the rapid decomposition of the peroxide compound and additional foaming action not related to the foaming agent; and
   the final pH of the combination of the first and second components is between about 6 and 6.5.

2. An effervescent foamable composition as in claim 1 wherein the first and second components are maintained separately until use.

3. An effervescent foamable composition as in claim 1 wherein the first and second components are-each liquids.

4. A foamable composition as in claim 1 wherein one or both of the first and second components further includes an oxidizing whitener, a peroxide or a peracetic acid.

5. A foamable composition as in claim 1 wherein one or both of the first and second components further includes a peroxide in an amount of about 1% (w/w) to about 50% (w/w).

6. A foamable composition as in claim 1 wherein one or both of the first and second components further includes a peroxide, and wherein said peroxide comprises metal ion free peroxide compounds.

7. A foamable composition as in claim 1 wherein one or both of the first and second components further includes a peroxide, and wherein said peroxide is selected from the group consisting of hydrogen peroxide, urea peroxide (carbamide peroxide), calcium peroxide, glyceryl peroxide, benzoyl peroxide and mixtures thereof.

8. A foamable composition as in claim 1 wherein one or both of the first and second components further includes a peroxide, and wherein the peroxide is present in one of from about 10% by weight to about 45% by weight of the first component, and from about 5% by weight to about 35% by weight of the second component.

9. A foamable composition as in claim 1 wherein the alkaline source of the second component is one or more of an effervescent, a carbonate, an alkali metal carbonate and a bicarbonate.

10. A foamable composition as in claim 1 wherein said second component includes a component selected from the group consisting of surfactants, alkali metal carbonates and bicarbonates, gas and mixtures thereof.

11. A foamable composition as in claim 1 wherein said surfactant comprises one or both of ionic and non-ionic surfactants.

12. A foamable composition as in claim 1 wherein said surfactant is selected from the group consisting of a sodium lauryl sulfate, a phospholipid, a low viscosity poloxamer, hydroxyethyl cellulose 4000-5000 CPS, a polysorbate, a pluronic F68 and a pluronic F88.

13. A foamable composition as in claim 1 wherein said second component is a foaming agent which comprises one or both of a hydrophilic and a hydrophobic component.

14. A foamable composition as in claim 1 wherein said first component comprises an acid selected from the group consisting of tartaric acid, and malic acid, and mixtures thereof.

15. The foamable composition of claim 1 wherein said peroxide activator is selected from the group consisting of a lower oxidative state transition metal salt, an alkali metal halide and combinations thereof.

16. A foamable composition as in claim 1 wherein said composition is free of agents that will tend to inhibit foaming.

17. A foamable composition as in claim 1 wherein said composition is free of carbon.

18. A foamable composition as in claim 1 wherein said composition is free of polymer.

19. A foamable composition as in claim 1 wherein said alkaline source is cocamidopropyl betaine.

20. A foamable composition as in claim 1 wherein said foam stabilizer further includes xanthan gum together with said hydroxyethyl cellulose.

\* \* \* \* \*